United States Patent
Numata et al.

(10) Patent No.: US 8,697,752 B2
(45) Date of Patent: *Apr. 15, 2014

(54) GREASE-LIKE GEL FOR REPELLING INSECTS AND PREVENTING UNDESIRABLE BEHAVIOR IN HOOFED ANIMALS

(75) Inventors: Richard Numata, Anaheim, CA (US); Ryan Willey, Huntington Beach, CA (US)

(73) Assignee: Pacific Tech Industries, Inc., Buena Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/439,631

(22) Filed: Apr. 4, 2012

(65) Prior Publication Data

US 2012/0252900 A1    Oct. 4, 2012

Related U.S. Application Data

(63) Continuation-in-part of application No. 13/082,323, filed on Apr. 7, 2011.

(60) Provisional application No. 61/322,779, filed on Apr. 9, 2010, provisional application No. 61/355,071, filed on Jun. 15, 2010.

(51) Int. Cl.
*A61K 31/16*    (2006.01)

(52) U.S. Cl.
USPC .......................................... 514/627

(58) Field of Classification Search
USPC .......................................... 514/627
See application file for complete search history.

(56) References Cited

U.S. PATENT DOCUMENTS

| | | | |
|---|---|---|---|
| 4,097,607 A * | 6/1978 | Larson | 514/627 |
| 4,827,064 A | 5/1989 | Wu | |
| 5,177,284 A | 1/1993 | Le et al. | |
| 5,457,254 A | 10/1995 | Ardito et al. | |
| 6,008,148 A | 12/1999 | Harris et al. | |
| 2005/0025796 A1 | 2/2005 | Nakamoto | |
| 2005/0058681 A1* | 3/2005 | Johnson | 424/405 |
| 2006/0110472 A1* | 5/2006 | Miron et al. | 424/754 |
| 2007/0218094 A1* | 9/2007 | Julier | 424/410 |
| 2009/0247441 A1 | 10/2009 | Baum | |

FOREIGN PATENT DOCUMENTS

| | | |
|---|---|---|
| JP | 2010031147 | 2/2010 |
| KR | 20100030801 | 3/2010 |
| WO | WO 2007/114825 A1 | 10/2007 |
| WO | WO2007114825 * | 10/2007 |

OTHER PUBLICATIONS

U.S. Appl. No. 13/267,728, filed Oct. 6, 2011, entitled Grease-Like Gel for Repelling Rodents, file history as of Jan. 28, 2013.

* cited by examiner

*Primary Examiner* — Rei-tsang Shiao
(74) *Attorney, Agent, or Firm* — Knobbe, Martens, Olson & Bear, LLP.

(57) ABSTRACT

Grease-like compositions are provided for repelling insects and preventing undesirable behavior in hoofed animals. The compositions utilize nontoxic mineral, synthetic, or vegetable oil based gels containing silica, clay, urea, polytetrafluoroethylene, or metallic soap thickeners and capsaicin.

23 Claims, No Drawings

GREASE-LIKE GEL FOR REPELLING INSECTS AND PREVENTING UNDESIRABLE BEHAVIOR IN HOOFED ANIMALS

CROSS-REFERENCE TO RELATED APPLICATIONS

This application is a continuation-in-part of U.S. patent application Ser. No. 13/082,323, filed Apr. 7, 2011, which claims the benefit of U.S. Provisional Application Ser. No. 61/322,779 filed Apr. 9, 2010 and U.S. Provisional Application No. 61/355,071 filed Jun. 15, 2010, the disclosures of which are hereby expressly incorporated by reference in their entirety and are hereby expressly made a portion of this application.

FIELD OF THE INVENTION

Grease-like compositions are provided for repelling insects and preventing undesirable behavior in hoofed animals. The compositions utilize nontoxic mineral, synthetic, or vegetable oil based gels containing silica, clay, urea, polytetrafluoroethylene, or metallic soap thickeners and capsaicin.

BACKGROUND OF THE INVENTION

Nontoxic insect repellents are a fast growing segment of the building improvement industry, food processing, and food preparation areas. Insects are carriers of communicable diseases, and thus preventing them from resting or congregating on the interior or exterior structures of public buildings is particularly important because of health and sanitation concerns.

Compositions that are effective in repelling insects, while exhibiting acceptable characteristics in terms of appearance, odor, and the like, are not readily formulated. If the composition has a strong repellent odor, it can actually be offensive to people within a short distance of the composition, thus reducing the likelihood that the composition will be tolerable in public places. If the repellent component is too weak or insufficiently dispersed in the composition, the composition will not be sufficiently effective. If a composition does not remain adhered to an insect's exoskeleton after initial contact, the repellent in the composition may not take full effect.

There are a number of products that have been employed to repel birds. In U.S. Patent Publication No. 2005-0025796, multiple repellent agents are used in a bird repellent composition. Capsaicin and menthol are used, in addition to carbomer gel, thickener, and water.

Another existing composition that contains capsaicin for repelling birds is marketed under the trademark Tanglefoot Bird Repellent™ by The Tanglefoot Company of Grand Rapids, Mich. It is composed of one repelling agent and one combined thickening, filling and dispersing agent. However, the composition lacks sufficient dispersion of the repelling agent because it has insufficient types of dispersal agents in the composition to provide maximum dispersal of the repellent. It also lacks sufficient tackifying qualities to sufficiently adhere the composition to the targeted species birds.

Nontoxic repellents for rodents (e.g., mice, rats, moles, voles, squirrels, chipmunks, and the like) are also commercially available. Such nontoxic formulations can emit the odor of predators (coyotes, foxes) or emit odors that are unpleasant to rodents (citronella, peppermint, menthol).

SUMMARY OF THE INVENTION

A grease-like gel that can be applied to any interior or exterior surface to deter insect infestation is of great practical convenience and economic advantage to the building industry. Nontoxic deterrents that provide long-lasting effect while not emitting an odor that is offensive to humans are also desirable.

In a first aspect, a method of repelling an insect is provided, comprising: applying a repelling composition to a surface, the repelling composition comprising 78.0 to 88.0 wt. % of a base oil selected from the group consisting of white oil, polyalphaolefins, glycols, polyalkylene glycols, alkylated naphthalenes, alkylated benzenes, esters and combinations thereof, 5.0 to 12.0 wt. % of a thickening agent, 5.0 to 10.0 wt. % of a tackifying polymer, 0.025 to 0.10 wt. % of a repellent agent selected from the group consisting of capsaicin, piperine, allyl isothiocyanate, allicin, and combinations thereof, and 1.0 to 2.0 wt. % of a solubility improving additive, whereby an insect is repelled from the surface.

In an embodiment of the first aspect, the base oil is white oil.

In an embodiment of the first aspect, the repellent agent is selected from the group consisting of capsaicin and piperine.

In an embodiment of the first aspect, the repelling composition comprises from 1.0-2.0 wt. % olefin copolymer as a component of the tackifying polymer.

In an embodiment of the first aspect, the thickening agent is selected from the group consisting of an inorganic or organic thickener.

In an embodiment of the first aspect, the inorganic thickener is selected from the group consisting of fumed silica, clay, and polytetrafluoroethylene.

In an embodiment of the first aspect, the organic thickener is selected from the group consisting of fatty acid complexes of aluminum, lithium, calcium, calcium sulfonate, sodium, titanium, and combinations thereof.

In an embodiment of the first aspect, the tackifying polymer is selected from the group consisting of polyisobutylene, polyalphaolefin, polybutene, and ethylene/propylene copolymer.

In an embodiment of the first aspect, the solubility improving additive is selected from the group consisting of hexane, chloroform, ethylacetate, ethyl ether, acetonitrile, acetone, and ethanol.

In an embodiment of the first aspect, the repelling composition comprises 83.9 wt. % of white oil; 10.0 wt. % of fumed silica; 5.0 wt. % of a tackifying polymer selected from the group consisting of polybutene, ethylene/propylene copolymer and polyisobutylene; 1.0 wt. % of ethanol; and 0.075 wt. % of capsaicin.

In an embodiment of the first aspect, the repelling composition comprises 78.0 to 88.0 wt. % of white oil, 5.0 to 12.0 wt. % of fumed silica, 5.0 to 10.0 wt. % of a tackifying polymer selected from the group consisting of polyisobutylene, polyalphaolefin, polybutene, ethylene/propylene copolymer, and combinations thereof, 0.025 to 0.10 wt. % of capsaicin, and 1.0 to 2.0 wt. % of ethanol.

In an embodiment of the first aspect, the repelling composition comprises 83.9 wt. % of white oil, 10.0 wt. % of fumed silica, 5.0 wt. % of polybutene, 1.0 wt. % of ethanol, and 0.075 wt. % of capsaicin.

In an embodiment of the first aspect, the repelling composition comprises 83.9 wt. % of white oil, 10.0 wt. % of fumed silica, 5.0 wt. % of polyisobutylene, 1.0 wt. % of ethanol, and 0.075 wt. % of capsaicin.

In an embodiment of the first aspect, the repelling composition comprises 83.9 wt. % of white oil, 10.0 wt. % of fumed silica, 5.0 wt. % of ethylene/propylene copolymer, 1.0 wt. % of ethanol, and 0.075 wt. % of capsaicin.

In an embodiment of the first aspect, the repelling composition comprises 82.9 wt. % of white base oil, 10.0 wt. % of a fumed silica, 5.0 wt. % of polyalphaolefin, 1.0 wt. % of olefin copolymer, 1.0 wt. % of ethanol, and 0.075 wt. % of capsaicin.

In an embodiment of the first aspect, the repelling composition comprises from 1.0-2.0 wt. % olefin copolymer as a component of the tackifying polymer.

In an embodiment of the first aspect, the repelling composition comprises 82.9 wt. % of white base oil, 10.0 wt. % of a fumed silica, 5.0 wt. % of polyalphaolefin, 1.0 wt. % of olefin copolymer, 1.0 wt. % of ethanol, and 0.075 wt. % of capsaicin.

In an embodiment of the first aspect, the insect is a cockroach.

In an embodiment of the first aspect, the insect is exterminated as a result of contacting the repelling composition.

In a second aspect, a method of repelling a hoofed animal is provided, comprising: applying a repelling composition to a surface, the repelling composition comprising 78.0 to 88.0 wt. % of a base oil selected from the group consisting of white oil, polyalphaolefins, glycols, polyalkylene glycols, alkylated naphthalenes, alkylated benzenes, esters and combinations thereof, 5.0 to 12.0 wt. % of a thickening agent, 5.0 to 10.0 wt. % of a tackifying polymer, 0.025 to 0.10 wt. % of a repellent agent selected from the group consisting of capsaicin, piperine, allyl isothiocyanate, allicin, and combinations thereof, and 1.0 to 2.0 wt. % of a solubility improving additive, whereby a hoofed animal is repelled from the surface.

In an embodiment of the second aspect, the base oil is white oil.

In an embodiment of the second aspect, the repellent agent is selected from the group consisting of capsaicin and piperine.

In an embodiment of the second aspect, the repelling composition comprises from 1.0-2.0 wt. % olefin copolymer as a component of the tackifying polymer.

In an embodiment of the second aspect, the thickening agent is selected from the group consisting of an inorganic or organic thickener.

In an embodiment of the second aspect, the inorganic thickener is selected from the group consisting of fumed silica, clay, and polytetrafluoroethylene.

In an embodiment of the second aspect, the organic thickener is selected from the group consisting of fatty acid complexes of aluminum, lithium, calcium, calcium sulfonate, sodium, titanium, and combinations thereof.

In an embodiment of the second aspect, the tackifying polymer is selected from the group consisting of polyisobutylene, polyalphaolefin, polybutene, and ethylene/propylene copolymer.

In an embodiment of the second aspect, the solubility improving additive is selected from the group consisting of hexane, chloroform, ethylacetate, ethyl ether, acetonitrile, acetone, and ethanol.

In an embodiment of the second aspect, the repelling composition comprises 83.9 wt. % of white oil; 10.0 wt. % of fumed silica; 5.0 wt. % of a tackifying polymer selected from the group consisting of polybutene, ethylene/propylene copolymer and polyisobutylene; 1.0 wt. % of ethanol; and 0.075 wt. % of capsaicin.

In an embodiment of the second aspect, the repelling composition comprises 78.0 to 88.0 wt. % of white oil, 5.0 to 12.0 wt. % of fumed silica, 5.0 to 10.0 wt. % of a tackifying polymer selected from the group consisting of polyisobutylene, polyalphaolefin, polybutene, ethylene/propylene copolymer, and combinations thereof, 0.025 to 0.10 wt. % of capsaicin, and 1.0 to 2.0 wt. % of ethanol.

In an embodiment of the second aspect, the repelling composition comprises 83.9 wt. % of white oil, 10.0 wt. % of fumed silica, 5.0 wt. % of polybutene, 1.0 wt. % of ethanol, and 0.075 wt. % of capsaicin.

In an embodiment of the second aspect, the repelling composition comprises 83.9 wt. % of white oil, 10.0 wt. % of fumed silica, 5.0 wt. % of polyisobutylene, 1.0 wt. % of ethanol, and 0.075 wt. % of capsaicin.

In an embodiment of the second aspect, the repelling composition comprises 83.9 wt. % of white oil, 10.0 wt. % of fumed silica, 5.0 wt. % of ethylene/propylene copolymer, 1.0 wt. % of ethanol, and 0.075 wt. % of capsaicin.

In an embodiment of the second aspect, the repelling composition comprises 82.9 wt. % of white base oil, 10.0 wt. % of a fumed silica, 5.0 wt. % of polyalphaolefin, 1.0 wt. % of olefin copolymer, 1.0 wt. % of ethanol, and 0.075 wt. % of capsaicin.

In an embodiment of the second aspect, the repelling composition comprises from 1.0-2.0 wt. % olefin copolymer as a component of the tackifying polymer.

In an embodiment of the second aspect, the repelling composition comprises 82.9 wt. % of white base oil, 10.0 wt. % of a fumed silica, 5.0 wt. % of polyalphaolefin, 1.0 wt. % of olefin copolymer, 1.0 wt. % of ethanol, and 0.075 wt. % of capsaicin.

In an embodiment of the second aspect, the hoofed animal is a horse.

In an embodiment of the second aspect, repelling the hoofed animal comprises deterring the hoofed animal from at least one undesirable behavior selected from the group consisting of cribbing, wood-chewing, and removing bandages.

In an embodiment of the second aspect, repelling the hoofed animal comprises deterring the hoofed animal from cribbing.

In an embodiment of the second aspect, repelling the hoofed animal comprises deterring the hoofed animal from removing bandages.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

A repellent composition based on a grease-like gel composition for use on exterior and interior surfaces of a structure, such as homes, restaurants, and office buildings is provided. The repellent composition is particularly preferred for use on insects (e.g., cockroaches, ants such as carpenter ants and moisture ants, clothes moths, silverfish, clover mites, bedbugs, termites, carpet beetles, crickets, fleas, dust mites, flies, golden buprestid, house centipede, mosquitoes, powder post beetles, psocids, booklice, spider beetles, granary and rice weevils, flour beetles, meal moths, firebrats, drug store beetles, saw-toothed grain beetles, and the like).

Unlike conventional repellents that rely on odiferous components such as menthol, the repellents of preferred embodiments rely on a different mechanism of action and thus can be odor-free. The repellents of preferred embodiments work by the insect making contact with the composition, which contains capsaicin, white pepper, or other components that produce a strong burning sensation in the mouth upon ingestion, but which are odorless or relatively odor-free. Use of menthol and other odiferous components conventionally employed in repellents is avoided, as such components can reduce the effectiveness of a gel repellent composition because it discourages insects from making physical contact with the composition.

Any of the repellents described herein are also effective at preventing undesirable behavior in hoofed animals (Ungulates), including perissodactyla, artiodactyla, tubulidentata, hyracoidean, sirenia, and proboscidea. For example, any of the repellents described herein can be used to prevent undesirable behavior in including horse, zebra, donkey, cattle, bison, rhinoceros, camel, hippopotamus, tapir, goat, pig, sheep, giraffe, okapi, moose, elk, deer, antelope, or gazelle. For example, any of the repellents described herein can be used to prevent undesirable behavior in horses.

The undesirable behavior that is deterred includes any behavior that causes damage to property or the hoofed animal. For example, the repellents described herein are capable of deterring hoofed animals from cribbing, wood-chewing, and removing bandages.

Repellent Additive

The repellent ingredient of the compositions of preferred embodiments is preferably capsaicin (8-methyl-N-vanillyl-6-nonenamide). It is the active component of chili peppers, which are plants belonging to the genus *Capsicum*. It is an irritant for mammals, including humans, and produces a sensation of burning in any tissue with which it comes into contact. Capsaicin and several related compounds are called capsaicinoids and are produced as a secondary metabolite by chili peppers. Pure capsaicin is a hydrophobic, colorless, odorless, crystalline to waxy compound. Capsaicin is the main capsaicinoid in chili peppers, followed by dihydrocapsaicin. These two compounds are also about twice as potent to the taste and nerves as the minor capsaicinoids nordihydrocapsaicin, homodihydrocapsaicin, and homocapsaicin. Besides the six natural capsaicinoids, one synthetic member of the capsaicinoid family exists, the vanillylamide of n-nonanoic acid. Table 1 provides a listing of several capsaicinoids.

TABLE 1

| Capsaicinoid name | Abbrev. | Scoville heat units | Chemical structure |
| --- | --- | --- | --- |
| Capsaicin | C | 16,000,000 | 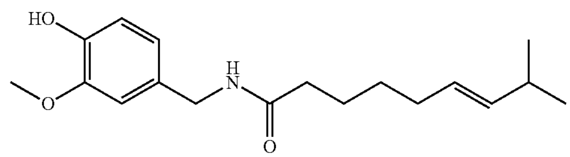 [SMILES: COc1cc(CNC(=O)CCCC/C=C/C(C)C)ccc1O] |
| Dihydrocapsaicin | DHC | 15,000,000 | 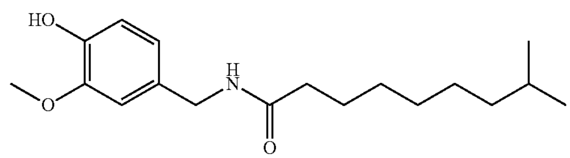 [SMILES: COc1cc(CNC(=O)CCCCCCC(C)C)ccc1O] |
| Nordihydrocapsaicin | NDHC | 9,100,000 | 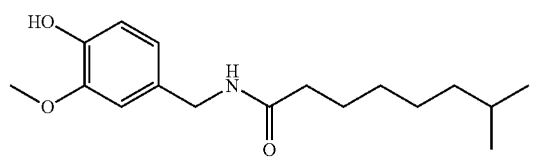 [SMILES: COc1cc(CNC(=O)CCCCCC(C)C)ccc1O] |
| Homodihydrocapsaicin | HDHC | 8,600,000 | 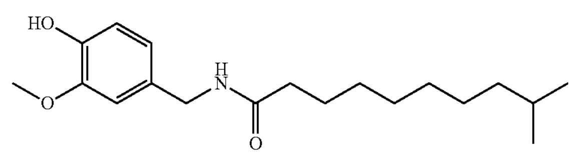 [SMILES: COc1cc(CNC(=O)CCCCCCCC(C)C)ccc1O] |
| Homocapsaicin | HC | 8,600,000 | 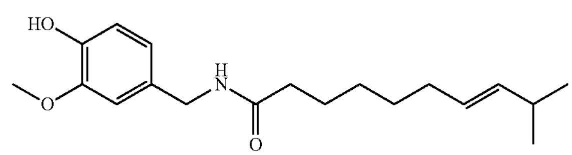 [SMILES: COc1cc(CNC(=O)CCCCC/C=C/C(C)C)ccc1O] |
| Nonivamide | PAVA | | 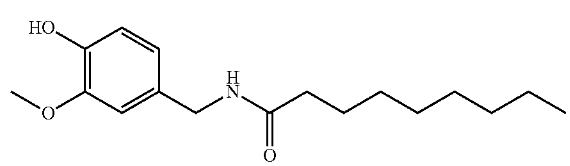 [SMILES: CCCCCCCCC(=O)NCc1ccc(O)c(OC)c1] |

Other components exhibiting similar properties can also be used as the repellent ingredient of the compositions of preferred embodiments. One such preferred component is piperine, the active piquant chemical in white and black pepper. Allyl isothiocyanate, the active piquant chemical in mustard, radishes, horseradish, and wasabi can also be employed, as can allicin, the active piquant flavor chemical in uncooked garlic and onions. A particularly preferred repellent additive is capsaicin, due to its lack of odor in purified form. Piperine also exhibits minimal odor in purified form. In applications where odor is not a concern, allyl isothiocyanate and allicin can advantageously be employed. While one repellent additive can advantageously be employed, combinations of two or more additives, e.g., capsaicin and piperine, are also suitable for use.

The repellent additive(s) typically comprise from about 0.005 wt. % or less to 0.5 wt. % or more of the repellent formulation, preferably from about 0.025 wt. % to about 0.1 wt. % of the repellent formulation.

Solubility Improving Additives

Repellent additives are preferably employed in purified form; however, in certain embodiments it can be acceptable to provide at least a portion of the repellent additive in a form of powdered vegetable product (e.g., chili powder). The repellent additive can be mixed into the grease base in powder or other solid form, or in a solubilized form.

To improve the solubility of the repellent additive or other additives in the grease formulation, in certain embodiments it can be preferred to add an activator agent or other solubility improver to the grease base (the term "solubility improving additive" as employed herein is used to collectively refer to both activator agents and solubility improvers). Esters, such as polyol esters can optionally be employed as solubility improving additives. Alternatively, if the repellent additive is provided in a purified form, the additive can be dissolved or dispersed in a suitable solvent, which is then mixed into the grease base. Suitable solvents for capsaicin include, e.g., hexane, chloroform, ethylacetate, ethyl ether, acetonitrile, acetone, and ethanol. Ethanol, petroleum ether, and dichloromethane are solvents for piperine. Allyl isothiocyanate and allicin are soluble in most organic solvents and are slightly soluble in water. While any suitable solvent for the repellent additive can be employed, if desired, ethanol, e.g., denatured ethanol, is generally preferred as the most environmentally acceptable activator agent. When ethanol is provided in denatured form, it can contain ethanol in combination with other additives. For example, the denatured ethanol may contain about 1-99% ethanol and about 1-99% additives, about 95% ethanol and about 5% additives, about 90% ethanol and about 10% additives, about 75% ethanol and about 25% additives, about 50% ethanol and about 50% additives. Additives employed in denatured alcohol include, for example, methanol, isopropyl alcohol, acetone, methyl ethyl ketone, methyl isobutyl ketone, and denatonium. In a preferred embodiment, the denatured ethanol contains 95% ethanol and 5% additives.

The solubility improving additive(s) typically comprise from about 0.25 wt. % or less to 5 wt. % or more of the repellent formulation, preferably from about 0.5 wt. % to about 3 wt. % of the repellent formulation, and more preferably from about 1 wt % to about 2 wt % of the repellent formulation.

Base Oil Carrier

The capsaicin or other repelling ingredient is provided in a grease-like base. Preferred grease-like bases include one or more base oil or fluid components as a carrier. The oil or base fluid may include any number of materials, which are typically divided into two groups: petroleum derived oils; and synthetic fluids, which are generally chemical reaction products. Petroleum derived oils include paraffinic oils, naphthenic oils, and aromatic oils. Synthetic fluids including polyalphaolefins, glycols, polyalkylene glycols, alkylated naphthalenes, alkylated benzenes, and esters have been used in compounding oil-based products.

It is generally preferred to employ base oils that are both low cost and exhibit low toxicity. Accordingly, light or heavy grade white oil (a transparent, colorless mineral oil composed mainly of C15-C40 alkanes and cyclic paraffins), preferably of a purity suitable for use in food or cosmetics, is preferably employed as a base oil. Alternatively, or in addition to mineral oil, vegetable oils can be utilized. Vegetable oils are lipids (esters) derived from plants. Suitable vegetable oils include, but are not limited to, coconut oil, corn oil, cottonseed oil, olive oil, palm oil, peanut oil, rapeseed oil, safflower oil, soybean oil, sunflower oil, almond oil, castor oil, cashew oil, hazelnut oil, macadamia oil, mongongo nut oil, pecan oil, pine nut oil, pistachio oil, walnut oil, bottle gourd oil, buffalo gourd oil, pumpkin seed oil, watermelon seed oil, acai oil, blackcurrant seed oil, borage seed oil, evening primrose oil, amaranth oil, apricot oil, apple seed oil, argan oil, artichoke oil, avocado oil, babassu oil, ben oil, borneo tallow nut oil, cape chestnut oil, carob pod oil, cassia oil, cocoa butter oil, cocklebur oil, cohune oil, coriander seed oil, dika oil, false flax oil, flax seed oil, grape seed oil, hemp oil, kapok seed oil, kenaf seed oil, lallemantia oil, marula oil, meadowfoam seed oil, mustard oil, nutmeg butter, okra seed oil, papaya seed oil, perilla seed oil, pequi oil, pine nut oil, poppyseed oil, prune kernel oil, quinoa oil, ramtil oil, rice bran oil, royle oil, sacha inchi oil, tea seed oil, thistle oil, tigernut oil, tomato seed oil, wheat germ oil, algae oil, copaiba, honge oil, jatropha oil, jojoba oil, milk bush, and petroleum nut oil.

Polyalphaolefins can be employed as base oil. Such polyalphaolefins include high viscosity polyalphaolefins as described in U.S. Pat. No. 4,827,064. For example, high viscosity polyalphaolefins possess a higher viscosity index than conventional polyalphaolefins of similar molecular weight. High viscosity polyalphaolefins generally exhibit higher film strengths than conventional viscosity polyalphaolefins are generally of higher viscosity than conventional polyalphaolefins of similar molecular weight, but exhibit lower pour points than the corresponding conventional polyalphaolefins. The lower pour point of high viscosity polyalphaolefins makes them suitable for use at lower temperatures than conventional polyalphaolefins. High viscosity polyalphaolefins also exhibit superior oxidative stability than conventional polyalphaolefins. High viscosity polyalphaolefins are characterized by a uniform molecular structure with low branch ratios. The branch ratio is the ratio of methyl ($—CH_3$) to methylene ($—CH_2—$) moieties in the molecular structure). High viscosity polyalphaolefins typically possess a branch ratio of less than about 0.19, while conventional polyalphaolefins branch possess a branch ratio greater than 0.2. The polymerization reaction by which high viscosity polyalphaolefins are formed is generally highly specific, resulting in a low number of isomers formed. The resulting high viscosity polyalphaolefin product oligomers have an atactic molecular structure of mostly head-to-tail attachments, with some head-to-head connections. High viscosity polyalphaolefins generally possess an average molecular weight of from about 300 to about 45,000, a carbon number of from about 30 to 1000, and a viscosity at 100° C. of about 3 to about 5000 cSt. The viscosity is typically in the range of about 150 to about 3000 cSt at 100° C. The branch ratio is typically less than 0.19. A high viscosity polyalphaolefin is marketed under the trade name SUPERSYN™ by Exxon Mobil Corporation of Houston, Tex.

Polyalphaolefin base oils suitable for use in formulations of preferred embodiments include EXXON Mobil Corporation's Spectrasyn™ line of polyalphaolefin fluid. Examples of Spectrasyn™ polyalphaolefin fluid include Spectrasyn™ 100, Spectrasyn™ 40, Spectrasyn™ 10, Spectrasyn™ 8, Spectrasyn™ 6, Spectrasyn™ 5, Spectrasyn™ 4, Spectrasyn™ 2C, and Spectrasyn™ 2. The viscosities of the Spectrasyn™ polyalphaolefin fluid vary. For example, Spectrasyn™ 100 and Spectrasyn™ 40 have relatively high viscosities. Spectrasyn™ 100 has a viscosity of 1240 cSt at 104° F., and Spectrasyn™ 40 has a viscosity of 396 cSt at 104° F. Spectrasyn™ 10, Spectrasyn™ 8, Spectrasyn™ 6, Spectrasyn™ 5, Spectrasyn™ 4, Spectrasyn™ 2C, and Spectrasyn™ 2 have relatively low viscosities. For example, Spectrasyn™ 10 has a viscosity of 66 cSt at 104° F., Spectrasyn™ 2 has a viscosity of 5 cSt at 104° F., Spectrasyn™ 2C has a viscosity of 6.4 cSt at 104° F., Spectrasyn™ 4 has a viscosity of 19 cSt at 104° F., Spectrasyn™ 5 has a viscosity of 25 cSt at 104° F., Spectrasyn™ 6 has a viscosity of 31 cSt at 104° F., and Spectrasyn™ 8 has a viscosity of 48 cSt at 104° F. The viscosity of the polyalphaolefin can be selected in order to achieve a formulation with desired characteristics. Generally, it is preferred to employ a high viscosity polyalphaolefin so as to provide greater structural integrity, weather resistance and stickiness to the repellant formulation.

Alkylated naphthalene is generally employed as additional base fluid to impart increased thermal and oxidative stability to a grease composition. See, e.g., U.S. Pat. No. 5,177,284 and U.S. Pat. No. 5,457,254. Mono or poly substituted alkylated naphthalenes can be employed. Similar to the alkylated naphthalenes are the polymers of alkyl benzenes, such as dodecylbenzenes, tetradecylbenzenes, dinonylbenzenes, di-(2-ethyl-hexyl)-benzenes, and the like. Alkylated aromatics are formed by the reaction of olefins or alkyl halides with aromatic compounds, such as benzene. Suitable alkylated naphthalenes can be obtained from EXXON Mobil Corporation.

Alkylated naphthalene fluids suitable for use in formulations of preferred embodiments include EXXON Mobil Corporation's Synesstic™ line of alkylated naphthalene. Examples of Synesstic™ alkylated naphthalene fluids include Synesstic™ 5 and Synesstic™ 12. Synesstic™ 12 alkylated naphthalene has a viscosity of 109 cSt at 104° F., and Synesstic™ 5 alkylated naphthalene has a viscosity of 29 cSt at 104° F.

One preferred class of synthetic fluid bases is that of synthetic polyolefins, particularly hydrogenated polyalphaolefins, although other synthetic polyolefins may be utilized as well. Examples of the synthetic hydrocarbon oils which may be utilized as additional synthetic fluid base oils for the formulations of preferred embodiments are preferably saturated. Such oils may be prepared by polymerizing unsaturated monomers (e.g., ethylene) and hydrogenating the resulting polymer prior to use to remove any residual unsaturation from the oil. Examples of the saturated hydrocarbon and halo-substituted hydrocarbon oils include polyethylenes, polypropylenes, polybutylenes, propylene-isobutylene copolymers, chlorinated polybutylenes, poly(1-hexenes), poly(1-octenes), poly(1-decenes); polyphenyls such as biphenyls, terphenyls, alkylated polyphenyls, and the like; alkylated diphenyl ethers and alkylated diphenyl sulfides and derivatives, including deuterated and hydrogenated derivatives. The hydrogenated polyolefins derived from alphaolefins such as ethylene, propylene, 1-butene, and the like are especially preferred for use as additional synthetic base oils. In certain embodiments, however, it may be preferred to use a polyolefin derived from a branched chain monomer, for example, isobutylene.

Dibasic acid esters can be employed as base oils. Polyol esters include molecules containing two or more alcohol moieties, such as trimethylolpropane, neopentylglycol, and pentaerythritol esters. Synthetic polyol esters are the reaction product of a fatty acid (e.g., derived from either animal or plant sources) and a synthetic polyol. Polyol esters have excellent thermal stability and generally resist hydrolysis and oxidation better than other base stocks. Naturally occurring triglycerides and vegetable oils, as discussed above, are in the same chemical family as polyol esters.

Trimethylolpropane esters may include mono, di, and tri esters. Neopentyl glycol esters may include mono and di esters. Pentaerythritol esters include mono, di, tri, and tetra esters. Dipentaerythritol esters may include up to six ester moieties. Preferred esters are typically of those of long chain monobasic fatty acids. Esters of C20 or higher acids can be employed, e.g., gondoic acid, eicosadienoic acid, eicosatrienoic acid, eicosatetraenoic acid, eicosapentanoic acid, arachidic acid, arachidonic acid, behenic acid, erucic acid, docosapentanoic acid, docosahexanoic acid, or ligniceric acid, or esters of C18 or lower acids, e.g., butyric acid, caproic acid, caprylic acid, capric acid, lauric acid, myristoleic acid, myristic acid, pentadecanoic acid, palmitic acid, palmitoleic acid, hexadecadienoic acid, hexadecatienoic acid, hexadecatetraenoic acid, margaric acid, margroleic acid, stearic acid, linoleic acid, octadecatetraenoic acid, vaccenic acid, or linolenic acid. In certain embodiments, it may be preferred to esterify pentaerythritol with a mixture of different acids. Particularly preferred synthetic ester oils are the esters of trimethylol propane, trimethylol butane, trimethylol ethane, pentaerythritol and/or dipentaerythritol with one or more monocarboxylic acids containing from about 5 to 10 carbon atoms.

Polyol polyesters may be obtained by reacting various polyhydroxy compounds with carboxylic acids. When the carboxylic acids are dicarboxylic acids, monohydroxy compounds can be substituted for the polyols. For example, synthetic esters include the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, and the like. These dicarboxylic acids may be reacted with alcohols such as, for example, butanol, hexanol, dodecyl alcohol, 2-ethylhexyl alcohol, and the like. Specific examples of such esters include dibutyl adipate, di(2-ethylhexyl)sebacate, di-N-hexyl fumarate, dioctyl sebacate, diisooctyl azelate, diisodecyl azelate, dioctyl phthalate, didecyl phthalate, and the like.

Silicon-based oils including siloxanes, such as polyalkylsiloxane, polyarylsiloxane, polyalkoxysiloxane, and polyaryloxysiloxane oils and silicone oils may also be suitable for use as additional base oils. Specific examples of some suitable polysiloxanes include methyl phenyl silicone, methyl tolyl silicone, methyl ethylphenyl silicone, ethyl phenyl silicone, propyl phenyl silicone, butyl phenyl silicone, and hexyl propylphenyl silicone. Preferred silicon-based oils also include silicones such as alkyl phenyl silicones. Preferred alkyl groups for alkyl phenyl silicones include aliphatic groups, e.g., methyl, propyl, pentyl, hexyl, decyl, and the like; alicyclic groups, e.g., cyclohexyl, cyclopentyl, and the like; aryl groups, e.g., phenyl, naphthyl, and the like; aralkyl groups; and alkaryl groups, e.g., tolyl, xylyl, and the like; and halogenated, oxygen-containing, and nitrogen-containing organyl groups such as halogenated aryl groups, alkyl and aryl ether groups, aliphatic ester groups, organic acid groups, cyanoalkyl groups, and the like. The alkyl groups preferably contain from 1 to about 30 carbon atoms. Alkyl phenyl silicones are particularly preferred. Alkyl phenyl silicones are particularly preferred, especially those having a viscosity of from about 20, 25, 50, 75, 100, 125, or 150 cSt to about 200, 250, 500, 750, 1000, 1250, 1500, 1750, or 2000 cSt at 25° C.

Particularly preferred base oils for use in formulations of preferred embodiments include Dow Corning® Brand Silicone Fluids. Silicone fluids from Dow Corning are high-performance, liquid lubricating materials that demonstrate excellent performance over a wide temperature range. Dow Corning® 200 Fluid, a dimethyl silicone fluid, is available in a range of viscosities (10 cSt or lower to 1,000 cSt or higher). Dow Corning® 510 Fluid, a phenyl methyl silicone fluid, is available in 50 cSt or lower to 30,000 cSt or higher viscosities. It functions over a wide range of ambient temperatures (from −51° C. to 204° C.). Dow Corning® 550 Fluid is a 125 CS phenyl methyl silicone fluid. It resists oxidation and has a wide service temperature range (from −40° C. to 232° C.). Dow Corning® 710 Fluid is a 500 CS phenyl methyl silicone fluid with excellent heat stability and resistance to evaporation and oxidation, and functions over a wide temperature range (from −18° C. to 260° C.). Dow Corning® FS-1265 Fluid is a fluorosilicon fluid with a viscosity of from 300 cSt or less to 10,000 cSt or more. It resists oxidation, harsh chemicals, fuels, and high temperatures, and functions over a temperature range of from −40° C. to 204° C.).

Particularly preferred white, off-white, and translucent white base oils for use in formulations of preferred embodiments include Dow Corning® Brand Silicone Fluids. Dow Corning® Brand Silicone Fluids are available in light to heavy consistencies. For example, Dow Corning® 7 Release Compound is a white-translucent light consistency dimethyl silicone compound with a service temperature range of −40° C. to 204° C. and a specific gravity at 25° C. of 1.0. Dow Corning® 4 Electrical Insulating Compound is a white-translucent medium consistency dimethyl silicone compound with a service temperature range of −57° C. to 204° C. and a specific gravity at 25° C. of 1.0. Dow Corning® 111 valve lubricant and sealant is a white-translucent heavy consistency dimethyl silicone compound with a service temperature range of −40° C. to 204° C. and a specific gravity at 25° C. of 1.0. The FDA has permitted Dow Corning® 4 and 7 Electrical Insulating Compounds and Dow Corning® 111 valve lubricant and sealant for food contact and they are listed under NSF Standard 51 for food processing, and NSF 51 for potable water applications. Another white, off-white, or translucent white base oil for use in formulations of preferred embodiments is Dow Corning® 112 high performance lube/sealant. Dow Corning® 112 sealant is a white-translucent stiff grease-like silicone compound containing an inert amorphous silica filler in combination with selected polydimethyl silicone fluids. Dow Corning® 112 has a specific gravity at 25° C. of 1.1. serviceability from −40° C. to 232° C., excellent water and oil resistance, good resistance to most chemicals, and low volatility.

Instead of or in addition to a base oil, a grease can be employed in formulations of preferred embodiment. Such greases typically comprise a base oil and a thickener. Particularly preferred greases are designated as suitable for food contact or processing, or potable water applications. Dow Corning's® Molycote® BG 20 High Performance Synthetic Grease is an example of a grease that can be used instead of or in addition to a base oil in formulations of preferred embodiments. Molycote® BG 20 High Performance Synthetic Grease is a beige synthetic polyolester grease with lithium complex thickener. Molycote® BG 20's properties include a wide temperature range if −45° C. to 182° C.

Polyethers suitable for use as base oils may include polyphenyl ether fluids, preferably those containing from 3 to 7 benzene rings and from 2 to 6 oxygen atoms, wherein the oxygen atoms link the benzene rings, which may be hydrocarbyl-substituted. The hydrocarbyl substituents are preferably free of unsaturated hydrocarbon groups. The preferred aliphatic substituents include saturated hydrocarbon groups containing from 1 to 6 carbon atoms, such as ethyl, propyl, butyl, and t-butyl groups. Preferred aromatic substituents include aryl groups such as phenyl, tolyl, t-butyl phenyl, and alphacumyl. Polyphenyl ethers consisting exclusively of chains of from 3 to 7 benzene rings with at least two oxygen atom joining the benzene rings exhibit superior thermal stability, for example, the polyphenyl ethers such as 1-(p-methylphenoxy)-4-phenoxy benzene and 2,4-diphenoxy-1-methyl benzene; 4-ring polyphenyl ethers such as bis[p-(p-methylphenoxy)phenyl]ether and bis[p-(p-t-butylphenoxy)phenyl]ether, and the like.

Polyalkylene glycols (also referred to as polyalkylene oxides) are polymers of alkylene oxides. Polyalkylene oxides and derivatives thereof wherein the terminal hydroxyl groups have been modified by esterification, etherification, and the like, also constitute a class of synthetic lubricating oils that can be utilized as a component of the base oil. These oils include those prepared through polymerization of ethylene oxide and propylene oxide, the alkyl and aryl ethers of these polyoxyalkylene polymers such as methyl polyisopropylene glycol ether having an average molecular weight of about 1000, diphenyl ether of polyethylene glycol having a molecular weight of about 500 to 1000, and diethyl ether of polypropylene glycol having a molecular weight of about 1000 to about 1500. Polyalkylene glycols suitable for use in formulations of preferred embodiments include PLURASAFE® Brand Silicone Fluids from BASF.

The base fluid may contain as its sole component a single base oil or a mixture of two or more base oils (e.g., of different chemical compositions or same category but different characteristics, e.g., different viscosities, viscosity indexes, molecular weights, produced by different manufacturing processes, and the like). In certain embodiments, however, it may be preferred to combine one or more high viscosity polyalphaolefins with one or more other mineral or synthetic base fluids.

The base oil(s) and/or base fluid(s) typically comprise from about 70 wt. % or less to about 95 wt. % or more of the repellent formulation, preferably from about 75 wt. % to about 90 wt. % of the repellent formulation.

Thickener

The base oil is thickened into a grease base by addition of a thickener. Thickener systems that can be advantageously employed include fumed silica, hydrophobic fumed silica, modified clay, dye and pigment thickeners, thickeners such as carbon black, graphite, polytetrafluoroethylene (PTFE), polyurea, and the like. The thickener can be added to the base oil using methods conventionally employed for preparing greases. Generally, a base oil is provided, or a blend of base oils is prepared, and then the thickener is added to the base oil with mixing.

Silica gel is advantageously employed as it can increase the adhesiveness of the composition, thereby increasing the time of contact between the composition and the target insect or hoofed animal. Silica gel is a granular, vitreous, highly porous form of silica. Silica gel is commonly employed as a food grade desiccant. Fumed silica, also known as pyrogenic silica, is a non-crystalline, fine-grain, low density and high surface area silica. Fumed silica has a very strong thickening effect. Primary particle size is 5-50 nm. The particles are non-porous and have a surface of 50-600 m²/g. Density 2.2 g/cm³. Fumed silica is made from flame pyrolysis of silicon tetrachloride or from quartz sand vaporized in a 3000° C. electric arc. Fumed silica serves as a universal thickening agent, a thickener in milkshakes, and an anticaking agent in powdered foods. Like silica gel, it serves as a desiccant. Hydrophobic silica is a silica that has hydrophobic groups chemically bonded to the surface. Hydrophobic silica can be made both from fumed and precipitated silica. The hydrophobic groups are normally alkyl or polydimethylsiloxane chains. The toxicological properties of silicas make them desirable thickening agents for the grease bases of preferred embodiments.

Fumed silicas suitable for use in formulations of preferred embodiments include AEROSIL 972™ manufactured by Degussa Corporation of Orange, Calif. or CABOSIL TS720™ manufactured by Cabot Corporation of Boston, Mass. AEROSIL 972™ is a hydrophobic fumed silica after treated with dimethyldichlorosilane. AEROSIL 972™ has a specific surface area of about 110±20 m²/g, an approximate tamped density of about 50 g/l, and an average primary particle size of about 16 nm. It is preferable that when using AEROSIL 972™, it is preferably present in the repellent formulation at from about 5.0 to 12.0 wt. %, and more desirably at about 10.0 wt. %. CABOSIL TS720™ is an insoluble white powder having a density of 2.2 g/cm³ at 20° C. It is preferable that when using CABOSIL TS720™, it is preferably present in the repellent formulation at from about 5.0 to 12.0 wt. %, and more desirably at about 10.0 wt. %.

Soap thickeners prepared by combining one or more fatty acids with one or more metal metal-containing components, e.g., alkali or alkaline earth metal hydroxides, oxide and/or isopropoxides can also be advantageously employed as low cost, low toxicity additives. When a soap thickener is employed, the soap itself can be added to the base oil, or the reactants yielding the soap can be added separately to the base oil and allowed to react. In certain embodiments it can be desirable to alter the mixing process and/or parameters, or the sequence of addition of components, as is appreciated by one skilled in the art. For example, the reactants yielding the soap may be added separately to different base oil components, or different portions of the base oil blend, then the partially additized blend components may be mixed. When reactants yielding soap are employed, the reactants are typically added to the base oil blend, and the mixture is heated to saponify the grease. After the saponification reaction reaches a sufficient degree of completion, the grease is allowed to cool and the remaining additives are incorporated into the grease.

Preferred metal containing components include alkaline earth metal hydroxides, such as calcium hydroxide, which exhibits good water resistance. Preferred fatty acids generally include those obtained from vegetable sources which contain from 10 to 22 carbon atoms. A single fatty acid or two or more fatty acids can be employed. Fatty acids containing 18 carbon atoms are particularly preferred, especially stearic acid or 12-hydroxy stearic acid; however, other fatty acids can advantageously be employed, including but not limited to gondoic acid, eicosadienoic acid, eicosadienoic acid, eicosatetraenoic acid, eicosapentanoic acid, arachidic acid, arachidonic acid, behenic acid, erucic acid, docosapentanoic acid, docosahexanoic acid, ligniceric acid, butyric acid, caproic acid, caprylic acid, capric acid, lauric acid, myristoleic acid, myristic acid, pentadecanoic acid, palmitic acid, palmitoleic acid, hexadecadienoic acid, hexadecatienoic acid, hexadecatetraenoic acid, margaric acid, margroleic acid, stearic acid, linoleic acid, octadecatetraenoic acid, vaccenic acid, and linolenic acid. One or more or more additional fatty acids may be employed to provide a more complex structure to the grease with increased cross-linking. Although, higher molecular weight acids can provide additional lubricity to the grease, they are generally inferior as additional complexing acids. Accordingly, one or more lower molecular weight fatty acids are used, preferably fatty acids containing from 2 to 10 carbon atoms, so as to provide greater cross-linking. Especially preferred is acetic acid.

To form the grease, the preferred alkaline earth (e.g., calcium) oxide or hydroxide is added to the base oil blend. Then, the fatty acids are added. The saponification reaction occurs upon heating the metal and fatty acids to a suitable temperature, typically about 175° C. The elevated temperature is then maintained, e.g., for about 20 minutes or until the reaction proceeds to a satisfactory degree of completion. The mixture is preferably stirred, either continuously or intermittently, during heating. After the resulting soap-containing mixture is cooled, the remaining additives are added. The preferred metal complex soap thickener is a calcium complex in which the fatty acid complex is formed by the reaction of calcium hydroxide with several organic acids including acetic acid and 12-hydroxystearic acid.

The thickener(s) typically comprise from about 3 wt. % or less to 20 wt. % or more of the repellent formulation, preferably from about 4 wt. % to about 15 wt. % of the repellent formulation.

Tackifiers

The base greases of preferred embodiments may contain various polymers which function as tackifying agents. The addition of polymers may add to the viscosity and also to the adhesive qualities of the composition so that the composition can be applied to both horizontal and vertical surfaces. The ability to apply the composition to vertical surfaces enhances its utility because this increases the potential number of surfaces on which the composition may be used. Useful tackifying agents include polymers like polybutene, polybutylene (e.g., polyisobutylene), olefin copolymers, methacrylates, polyalphaolefins, and ethylene/propylene copolymers. Food grade tackifiers are particularly preferred. Tackifiers are generally provided in a suitable carrier, e.g., paraffinic oil, naphthenic oil, while oil, or polyalphaolefin, and can include polyisobutylene in white mineral oil and have a viscosity of, e.g., 2500 cSt @ 100° C. or more (e.g., 3000 or 4000 cSt @ 100° C.).

The tackifier(s) typically comprise from about 2.0 wt. % or less to 20 wt. % or more of the repellent formulation, preferably from about 3 wt. % to about 15 wt. % of the repellent formulation.

Other Additives

Other additives as are known in the lubricating arts may also be employed in the base greases of preferred embodiments. These include metal deactivators such as benzotriazole, substituted benzotriazole and 2,5-di-mercapto-1,3,4-thiodiazole, which protect ferrous and nonferrous metal surfaces from corrosion. The base grease can also include conventional fillers, thickeners, thixotropic agents, antioxidants, corrosion prevention materials, and the like, depending upon the surface to which the repellent formulation is to be applied. Solid lubricant components can be added at any suitable step in the grease manufacturing process, for example, when the thickener is added if the thickener is not a metal soap type which is formed by a chemical reaction in the oil. Solid additives are preferably added to the grease with sufficient mixing, working, homogenizing, or the like, to ensure a complete, uniform, and thorough dispersion of solid particles. Preferably, solid lubricants are added to the grease after the thickener is formed or added.

Various compounds known for use as oxidation inhibitors can be utilized in grease formulations of various embodiments, advantageously when the compositions are to be employed in contact with oxidation-sensitive materials. These include phenolic antioxidants, amine antioxidants, sulfurized phenolic compounds, and organic phosphites, among others. Is it especially preferred that the antioxidant includes predominately or entirely either a hindered phenol antioxidant such as 2,6-di-tert-butylphenol, 4-methyl-2,6-di-tert-butylphenol, 2,4-dimethyl-6-tert-butylphenol, 4,4'-methylenebis(2,6-di-tert-butylphenol), and mixed methylene bridged polyalkyl phenols, or an aromatic amine antioxidant such as the cycloalkyl-di-lower alkyl amines (N,N'-di-lower-alkyl phenylenediamines, such as N,N'-di-sec-butyl-p-phenylenediamine, and its analogs), and phenylenediamines, or a combination of one or more such phenolic antioxidants with one or more such amine antioxidants.

A variety of corrosion inhibitors are also available for use in the grease formulations of various embodiments, advantageously when the compositions are to be employed in contact with corrosion-sensitive materials. Corrosion inhibitors include dimer and trimer acids, such as are produced from tall oil fatty acids, oleic acid, linoleic acid, and the like. Other useful types of corrosion inhibitors are the alkenyl succinic acid and alkenyl succinic anhydride corrosion inhibitors such as, for example, tetrapropenylsuccinic acid, tetrapropenylsuccinic anhydride, tetradecenylsuccinic acid, tetradecenylsuccinic anhydride, hexadecenylsuccinic acid, hexadecenylsuccinic anhydride, and the like. Also useful are the half esters of alkenyl succinic acids having 8 to 24 carbon atoms in the alkenyl group with alcohols such as the polyglycols. Also useful are the aminosuccinic acids or derivatives. Preferably a dialkyl ester of an aminosuccinic acid is used containing an alkyl group containing 15-20 carbon atoms or an acyl group which is derived from a saturated or unsaturated carboxylic acid containing 2-10 carbon atoms. Most preferred is a dialkylester of an aminosuccinic acid.

The various additives that can be included in the base greases of preferred embodiments are used in conventional amounts as are known in the grease industry. The amounts used in any particular case are preferably sufficient to provide the desired functional property to the grease composition, and such amounts are well known to those skilled in the art.

Repellent Formulations

The repellent formulations of preferred embodiments typically include a carrier agent, an activator agent, a repellent, a thickener, and a tackifying agent, as described above. In some embodiments, the activator agent, the carrier agent, and/or the tackifying agent may be omitted from the composition.

Preferably, the repellent formulation utilizes a white oil. White oils include any of various highly refined, colorless mineral or hydrocarbon oils of low volatility and a wide range of viscosities. They are typically used for lubrication of food and textile machinery and as medicinal and mineral oils. White oils include technical white oils such as USP or Technical Grade white oil, and can be used as a carrier agent/base oil in formulations of preferred embodiments. In such embodiments, the white oil is typically present at from about 78.0 to 88.0 wt. % in the formulation, and more desirably at about 83.9 wt. %. In other embodiments, white oil is desirably present at about 82.9 wt. % in the formulation. The repellent formulation preferably utilizes fumed silica, such as AEROSIL 972™ manufactured by Degussa Corporation of Orange, Calif. or CABOSIL TS720™ manufactured by Cabot Corporation of Boston, Mass. When using AEROSIL 972™, it is preferably present in the repellent formulation at from about 5.0 to 12.0 wt. %, and more desirably at about 10.0 wt. %. When using CABOSIL TS720™, it is preferably present in the repellent formulation at from about 5.0 to 12.0 wt. %, and more desirably at about 10.0 wt. %. The repellent composition preferably includes one or more tackifying polymers, preferably an olefin copolymer, polybutene, polyalphaolefin, or polymethacrylate of suitable viscosity. The tackifying agent is preferably present in the formulation in total at from 5.0 to 10.0 wt. %, and more desirably at about 5.0 wt. %. The repellent composition preferably includes an activator agent such as denatured ethanol. When using denatured ethanol, it is preferably present in the formulation in total at from 1.0 to 2.0 wt. %, and more desirably at about 1.0 part by weight. The repellent additive in the repellent composition is preferably natural capsaicin. When using natural capsaicin, it is preferably present in the formulation in total at from 0.025 to 1.00 wt. %, and more desirably at about 0.075 wt. %. Preferably, the repellent compositions of preferred embodiments contain no menthol, peppermint oil, citronella, or other components that repel insects and hoofed animals by emitting an odor that insects and hoofed animals find offensive.

The repellent composition may preferably include one or more tackifying polymers, preferably an olefin copolymer, polybutene, polyalphaolefin, or polymethacrylate of suitable viscosity. In some embodiments, the repellent formulation utilizes two different tackifiers, preferably polyalphaolefin and an olefin copolymer. In such a preferred embodiment, the tackifiers are preferably present in the formulation in total at from about 0.05 wt. % to about 10.0 wt. %. More preferably polyalphaolefin is present in the formulation at about 5.0 wt. % and an olefin copolymer is present in the formulation at about 1.0 wt. %. In preferred embodiments where polyalphaolefin is present in the formulation at about 5.0 wt. % and an olefin copolymer is present in the formulation at about 1.0 wt. %, the white oil is preferably present at about 82.9 wt. %.

EXAMPLES

Although the repellent compositions of preferred embodiments can be made by various methods as will be appreciated by one of skill in the art, the following is an exemplary method for use in preparing a repellent composition of a preferred embodiment comprising technical grade white oil, denatured ethanol, fumed silica, tackifying polymer, and capsaicin. In a first step, the full amount of technical grade white oil is added to a mixer. In a next step, denatured ethanol and fumed silica are sequentially or concurrently added to the white oil while mixing. Next, the mixture is heated up to about 120° F. (49° C.). The mixture is maintained at this temperature while mixing until the fumed silica is completely or nearly completely dispersed and the mixture clear. Thereafter, the polymer tackifier is added while mixing and maintaining the mixture at about 120° F. (49° C.). Mixing at about 120° F. (49° C.) is continued until the polymer is completely or nearly completely dissolved and the mixed product is clear. Then, the capsaicin is completely mixed in, and the product is cooled down to about 120° F. (27° C.). The repellent composition thus prepared is stable at ambient temperatures in environments supporting insects and hoofed animals.

The examples below list different exemplary formulations for the deterrent composition of preferred embodiments. In the examples below, the column "Component" lists exemplary ingredients for the composition, the column "Mass %" lists desirable parts by weight of the ingredients in the composition and the column "Range Mass %" lists exemplary parts by weight of the ingredients. The asterisk "*" indicates that the base oil component is added to bring the total mass % up to 100%, after the other ingredients are accounted for.

Example 1

| Component | Mass % | Range Mass % |
|---|---|---|
| Technical Grade/USP White Oil | 82.925 | 78.0-88.0 |
| Denatured Ethanol | 1.0 | 1.0-2.0 |
| Capsaicin (Natural) | 0.075 | 0.025-0.075 |
| Aerosil 972 Fumed Silica | 10.0 | 5.0-12.0 |
| PAO | 5.0 | 5.0-10.0 |
| Olefin Copolymer/Tackifier | 1.0 | 1.0-2.0 |

Example 2

| Component | Mass % | Range Mass % |
|---|---|---|
| Technical Grade/USP White Oil | 82.925* | 78.0-88.0 |
| Denatured Ethanol | 1.0 | 1.0-2.0 |
| Capsaicin (Natural) | 0.075 | 0.025-0.075 |
| CabOSil TS-720 | 10.0 | 5.0-12.0 |
| Olefin Copolymer/Tackifier | 1.0 | 1.0-2.0 |
| PAO | 5.0 | 5.0-10.0 |

Example 3

| Component | Mass % | Range Mass % |
|---|---|---|
| Technical Grade/USP White Oil | 83.925* | 78.0-88.0 |
| Denatured Ethanol | 1.0 | 1.0-2.0 |
| Capsaicin (Natural) | 0.075 | 0.025-0.075 |
| Aerosil 972 Fumed Silica | 10.0 | 5.0-12.0 |
| Polybutene | 5.0 | 5.0-10.0 |

Example 4

| Component | Mass % | Range Mass % |
|---|---|---|
| Technical Grade/USP White Oil | 83.925* | 78.0-88.0 |
| Denatured Ethanol | 1.0 | 1.0-2.0 |
| Capsaicin (Natural) | 0.075 | 0.025-0.075 |
| CabOSil TS-720 | 10.0 | 5.0-12.0 |
| Polybutene | 5.0 | 5.0-10.0 |

Example 5

| Component | Mass % | Range Mass % |
|---|---|---|
| Technical Grade/USP White Oil | 83.925* | 78.0-88.0 |
| Denatured Ethanol | 1.0 | 1.0-2.0 |
| Capsaicin (Natural) | 0.075 | 0.025-0.075 |
| Aerosil 972 Fumed Silica | 10.0 | 5.0-12.0 |
| Ethylene/Propylene Copolymer | 5.0 | 5.0-10.0 |

Example 6

| Component | Mass % | Range Mass % |
|---|---|---|
| Technical Grade/USP White Oil | 83.925* | 78-88 |
| Denatured Ethanol | 1.0 | 1.0-2.0 |
| Capsaicin (Natural) | 0.075 | 0.025-0.075 |
| CabOSil TS-720 | 10.0 | 5.0-12.0 |
| Ethylene/Propylene Copolymer | 5.0 | 5.0-10.0 |

The repellent compositions of preferred compositions can be applied to surfaces using similar techniques to application of caulk. A line, bead, or strip of the repellent composition is applied to a surface in an area where insects are to be repelled. When an insect contacts the repellent composition, e.g., by stepping on it, the repellent composition is transferred to the insect's exoskeleton. When the insect attempts to remove the repellent composition, e.g., by eating it off, the repellent additive in the repellent composition produces an unpleasant taste, thereby discouraging the insect from contacting the repellent composition again (e.g., attempting to cross a strip of the repellent composition).

The repellent compositions of preferred compositions can be applied to surfaces using similar techniques to application of caulk. A line, bead, or strip of the repellent composition is applied to a surface in an area where insects are desired to be repelled, or where hoofed animals exhibit undesirable behavior. When an insect contacts the repellent composition, e.g., by eating it, the repellent additive in the repellent composition produces an unpleasant taste, thereby discouraging the insect from contacting the repellent composition again. Similarly the repellent composition can prevent a hoofed animal from contacting the repellent composition again (e.g., using a treated area for cribbing).

The repellent compositions of preferred embodiments can offer numerous advantages over conventional repellent compositions. The repellent compositions of preferred embodiments can be odor free or low odor, enabling them to be employed in areas such as restaurants, stores, and homes where odors would otherwise be offensive or unacceptable. The repellent compositions of preferred embodiments are non-toxic and environmentally friendly, making them acceptable for use near soil or water sources (rivers, streams, canals, water features, ground water, etc.), or areas inhabited by children, pets (e.g., dogs, cats) or non-pest native species (e.g., native birds, mammals, reptiles, amphibians, fish). The repellent compositions of preferred embodiments are tacky, enabling them to remain in place when applied to non-horizontal surfaces (e.g., slanting, vertical, or inverted), and to persist on insects' exoskeletons or hoofed animal when contacted, which increases the repellent effect when the insects and hoofed animals groom themselves to remove the repellent composition. The repellent compositions of preferred embodiments are also water resistant, such that they can remain in place and retain their repellency when exposed to the elements (rain, snow). The repellent compositions of preferred embodiments are stable and maintain good viscosity/tackiness when exposed to hot or cold ambient conditions.

In further embodiments, the compositions described above can be used as an insect repellant and the methods described above can be used to repel insects. The repellant compositions can be any of the repellant compositions described above, including those containing capsaicin, piperine, allyl isothiocyanate, and/or allicin as a repellant additive. While one compositions containing one repellant additive can advantageously be employed, combinations of two or more additives, e.g., capsaicin and piperine, are also suitable for use. The compositions and methods described above are effective at repelling a large variety of insects, including fairly resilient insects such as cockroaches. The repellant additive can cause insects to be repelled from an area or exterminated in an area. In some embodiments, the insects are exterminated. The additive can exterminate insects through one or more of metabolic disruption, membrane damage, or nervous system dysfunction. Additionally, when formulated as an oil or grease, the composition can block the air holes (spiracles) through which insects breathe, causing them to die from asphyxiation. In some cases, oils also may act as poisons, interacting with the fatty acids of the insect and interfering with normal metabolism. Oils may also disrupt how the insect feeds.

In further embodiments, the compositions described above can be used to deter undesirable behavior in hoofed animals. The repellant compositions can be any of the repellant compositions described above, including those containing capsaicin, piperine, allyl isothiocyanate, and/or allicin as a repellant additive. While one compositions containing one repellant additive can advantageously be employed, combinations of two or more additives, e.g., capsaicin and piperine, are also suitable for use. The undesirable behavior includes cribbing, wood-chewing, and removing bandages. Cribbing is a behavior in which a hoofed animal may place its mouth on a solid object, arch its neck, and suck in air. This behavior can cause many health problems including colic and stomach ulcers. The compositions described above can be spread over solid objects that a hoofed animal may be tempted to use for cribbing or wood-chewing. Additionally, the compositions described above can be spread over bandages that are placed on a hoofed animal to prevent the hoofed animal from attempting to remove the bandages.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of repelling an insect, comprising:
applying a repelling composition to a surface, the repelling composition comprising 78.0 to 88.0 wt. % of a base oil selected from the group consisting of white oil, polyalphaolefins, glycols, polyalkylene glycols, alkylated naphthalenes, alkylated benzenes, esters and combinations thereof, 5.0 to 12.0 wt. % of a thickening agent, 5.0 to 10.0 wt. % of high viscosity polyalphaolefin, 0.025 to 0.10 wt. % of a repellent agent selected from the group consisting of capsaicin, piperine, allyl isothiocyanate, allicin, and combinations thereof, and 1.0 to 2.0 wt. % of a solubility improving additive, whereby an insect is repelled from the surface.

2. The method of claim 1, wherein the base oil is white oil.

3. The method of claim 1, wherein the repellent agent is selected from the group consisting of capsaicin and piperine.

4. The method of claim 1, wherein the repelling composition further comprises from 1.0-2.0 wt. % olefin copolymer.

5. The method of claim 1, wherein the thickening agent is selected from the group consisting of an inorganic or organic thickener.

6. The method of claim 1, wherein the inorganic thickener is selected from the group consisting of fumed silica, clay, and polytetrafluoroethylene.

7. The method of claim 1, wherein the organic thickener is selected from the group consisting of fatty acid complexes of aluminum, lithium, calcium, calcium sulfonate, sodium, titanium, and combinations thereof.

8. The method of claim 1, wherein the solubility improving additive is selected from the group consisting of hexane, chloroform, ethylacetate, ethyl ether, acetonitrile, acetone, and ethanol.

9. The method of claim 1, wherein the repelling composition comprises 83.9 wt. % of white oil; 10.0 wt. % of fumed silica; 5.0 wt. % of high viscosity polyalphaolefin; 1.0 wt. % of ethanol; and 0.075 wt. % of capsaicin.

10. The method of claim 1, wherein the repelling composition comprises 78.0 to 88.0 wt. % of white oil, 5.0 to 12.0 wt. % of fumed silica, 5.0 to 10.0 wt. % of high viscosity polyalphaolefin, 0.025 to 0.10 wt. % of capsaicin, and 1.0 to 2.0 wt. % of ethanol.

11. The method of claim 1, wherein the repelling composition comprises 82.9 wt. % of white base oil, 10.0 wt. % of a fumed silica, 5.0 wt. % of high viscosity polyalphaolefin, 1.0 wt. % of olefin copolymer, 1.0 wt. % of ethanol, and 0.075 wt. % of capsaicin.

12. The method of claim 1, wherein the insect is a cockroach.

13. The method of claim 1, whereby the insect is exterminated.

14. A method of repelling a hoofed animal, comprising:
applying a repelling composition to a surface, the repelling composition comprising 78.0 to 88.0 wt. % of a base oil selected from the group consisting of white oil, polyalphaolefins, glycols, polyalkylene glycols, alkylated naphthalenes, alkylated benzenes, esters and combinations thereof, 5.0 to 12.0 wt. % of a thickening agent, 5.0 to 10.0 wt. % of high viscosity polyalphaolefin, 0.025 to 0.10 wt. % of a repellent agent selected from the group consisting of capsaicin, piperine, allyl isothiocyanate, allicin, and combinations thereof, and 1.0 to 2.0 wt. % of a solubility improving additive, whereby a hoofed animal is repelled from the surface.

15. The method of claim 14, wherein the repelling composition comprises 83.9 wt. % of white oil; 10.0 wt. % of fumed silica; 5.0 wt. % of high viscosity polyalphaolefin; 1.0 wt. % of ethanol; and 0.075 wt. % of capsaicin.

16. The method of claim 14, wherein the repelling composition comprises 78.0 to 88.0 wt. % of white oil, 5.0 to 12.0 wt. % of fumed silica, 5.0 to 10.0 wt. % of high viscosity polyalphaolefin, 0.025 to 0.10 wt. % of capsaicin, and 1.0 to 2.0 wt. % of ethanol.

17. The method of claim 14, wherein the repelling composition comprises 82.9 wt. % of white base oil, 10.0 wt. % of a fumed silica, 5.0 wt. % of high viscosity polyalphaolefin, 1.0 wt. % of olefin copolymer, 1.0 wt. % of ethanol, and 0.075 wt. % of capsaicin.

18. The method of claim 14, wherein the repelling composition further comprises from 1.0-2.0 wt. % olefin copolymer.

19. The method of claim 14, wherein the repelling composition comprises 82.9 wt. % of white base oil, 10.0 wt. % of a fumed silica, 5.0 wt. % of high viscosity polyalphaolefin, 1.0 wt. % of olefin copolymer, 1.0 wt. % of ethanol, and 0.075 wt. % of capsaicin.

20. The method of claim 14, wherein the hoofed animal is a horse.

21. The method of claim 14, whereby the hoofed animal is deterred from at least one undesirable behavior selected from the group consisting of cribbing, wood-chewing, and removing bandages.

22. The method of claim 14, whereby the hoofed animal is deterred from cribbing.

23. The method of claim 14, whereby the hoofed animal is deterred from removing bandages.

* * * * *

UNITED STATES PATENT AND TRADEMARK OFFICE
CERTIFICATE OF CORRECTION

PATENT NO. : 8,697,752 B2  Page 1 of 1
APPLICATION NO. : 13/439631
DATED : April 15, 2014
INVENTOR(S) : Numata et al.

It is certified that error appears in the above-identified patent and that said Letters Patent is hereby corrected as shown below:

In the Specification

In column 10 at line 24, Change "ligniceric" to --lignoceric--.
In column 10 at line 28, Change "hexadecatienoic acid," to --hexadecatrienoic acid,--.
In column 10 at line 29, Change "margroleic acid," to --margaroleic acid,--.
In column 11 at line 64, Change "Molycote®" to --Molykote®--.
In column 11 at line 67, Change "Molycote®" to --Molykote®--.
In column 12 at line 2, Change "Molycote®" to --Molykote®--.
In column 13 at line 64, Change "ligniceric" to --ignoceric--.
In column 13 at line 67, Change "hexadecatienoic acid," to --hexadecatrienoic acid,--.
In column 14 at line 1, Change "margroleic acid," to --margaroleic acid,--.

Signed and Sealed this
Sixteenth Day of September, 2014

Michelle K. Lee
*Deputy Director of the United States Patent and Trademark Office*